(12) United States Patent
Brehm et al.

(10) Patent No.: US 11,147,606 B2
(45) Date of Patent: Oct. 19, 2021

(54) ENDOSCOPIC CUTTING DEVICE HAVING A CUTTING WIRE DIRECTED THROUGH OPENINGS IN A TUBE TO FORM TWO DIATHERMY BLADES, AND A PROBE FOR A PERCUTANEOUS ENDOSCOPIC GASTROSTOMY

(71) Applicant: FUJIFILM MEDWORK GMBH, Höchstadt/Aisch (DE)

(72) Inventors: Andreas Brehm, Adelsdorf (DE); Matthias Stirnweiss, Lonnerstadt (DE); Jörg Klyeisen, Heroldsbach (DE)

(73) Assignee: FUJIFILM MEDWORK GMBH, Höchstadt (DE)

( * ) Notice: Subject to any disclaimer, the term of this patent is extended or adjusted under 35 U.S.C. 154(b) by 362 days.

(21) Appl. No.: 15/552,573

(22) PCT Filed: Jan. 30, 2016

(86) PCT No.: PCT/DE2016/100038
§ 371 (c)(1),
(2) Date: Aug. 22, 2017

(87) PCT Pub. No.: WO2016/134693
PCT Pub. Date: Sep. 1, 2016

(65) Prior Publication Data
US 2018/0049793 A1    Feb. 22, 2018

(30) Foreign Application Priority Data
Feb. 23, 2015    (DE) ............... 10 2015 102 542.6

(51) Int. Cl.
*A61B 18/08*    (2006.01)
*A61B 1/00*    (2006.01)
(Continued)

(52) U.S. Cl.
CPC ........ *A61B 18/082* (2013.01); *A61B 1/00087* (2013.01); *A61B 17/00234* (2013.01);
(Continued)

(58) Field of Classification Search
CPC ... A61B 18/12; A61B 18/08; A61B 17/00234; A61B 1/00087; A61B 2017/00269;
(Continued)

(56) References Cited

U.S. PATENT DOCUMENTS

| 2,008,525 A | 7/1935 | Wolber et al. |
| 4,181,131 A | 1/1980 | Ogiu |

(Continued)

FOREIGN PATENT DOCUMENTS

| DE | 2426781 A1 | 12/1975 |
| JP | 53105888 A | 9/1978 |

(Continued)

OTHER PUBLICATIONS

Cyrany J. et al; New technique for release of a buried bumper . . . ; Endoscopy 2012; 44; E422-E423.

*Primary Examiner* — Ronald Hupczey, Jr.
(74) *Attorney, Agent, or Firm* — Lucas & Mercanti, LLP; Klaus P. Stoffel (57) ABSTRACT

An endoscopic cutting device for cutting free a probe, provided with a retaining plate, which, within the scope of a percutaneous endoscopic gastrostomy, is arranged in a stomach wall and is overgrown by the gastric mucosa, wherein, for the adjustment of the cutting element provided at a distal end of a tube via a pulling cord, an actuation force of an actuation element can be transmitted to same. In addition, the cutting device includes a cutting wire which is electrically heatable and connected to the pulling cord, and which runs outside the tube via a distal section to form a first diathermy blade. In addition, the distal end of the tube is
(Continued)

slanted at an angle to the transverse plane thereof to form a tip, wherein the tip is facing the first diathermy blade. Furthermore, the cutting wire is directed externally around the tip to form a second diathermy blade.

10 Claims, 4 Drawing Sheets

(51) Int. Cl.
    *A61B 17/00*     (2006.01)
    *A61B 18/00*     (2006.01)
    *A61B 17/32*     (2006.01)

(52) U.S. Cl.
    CPC .... *A61B 18/08* (2013.01); *A61B 2017/00269* (2013.01); *A61B 2017/00323* (2013.01); *A61B 2017/00946* (2013.01); *A61B 2017/00955* (2013.01); *A61B 2017/32006* (2013.01); *A61B 2018/00297* (2013.01); *A61B 2018/00494* (2013.01); *A61B 2018/00601* (2013.01); *A61B 2018/00982* (2013.01)

(58) Field of Classification Search
    CPC .......... A61B 2017/00323; A61B 2017/00946; A61B 2017/00955; A61B 2017/32006; A61B 2017/22038–22049; A61B 2018/00297; A61B 2018/00494; A61B 2018/00982; A61B 2018/144
    See application file for complete search history.

(56) References Cited

U.S. PATENT DOCUMENTS

| | | |
|---|---|---|
| 6,200,313 B1 | 3/2001 | Abe |
| 6,517,550 B1 * | 2/2003 | Konya .................. A61B 17/221 606/113 |
| 7,229,440 B2 | 6/2007 | Ho |
| 7,896,876 B2 | 3/2011 | Kawahara |
| 8,021,363 B2 | 9/2011 | Vakharia |
| 9,039,661 B2 | 5/2015 | Becker |
| 2003/0108853 A1 * | 6/2003 | Chosack ................ G06T 17/00 434/262 |
| 2007/0282358 A1 * | 12/2007 | Remiszewski ......... A61B 17/00 606/159 |
| 2008/0109022 A1 * | 5/2008 | Sherwood ........ A61B 17/32056 606/170 |
| 2009/0043259 A1 | 2/2009 | Hardin |
| 2009/0112226 A1 | 4/2009 | Self |
| 2012/0302962 A1 * | 11/2012 | Becker ................ A61J 15/0015 604/174 |
| 2013/0110126 A1 | 5/2013 | Mujwid |
| 2014/0243822 A1 | 8/2014 | Farin et al. |
| 2014/0276911 A1 * | 9/2014 | Smith .................... A61B 18/14 606/113 |
| 2014/0276949 A1 * | 9/2014 | Staunton .......... A61B 17/32002 606/130 |
| 2017/0143363 A1 * | 5/2017 | Dormann ....... A61B 17/320016 |

FOREIGN PATENT DOCUMENTS

| | | |
|---|---|---|
| JP | H02141428 U | 11/1990 |
| JP | H07265329 A | 10/1995 |
| JP | H1082946 A | 3/1998 |
| JP | 11113924 A | 4/1999 |
| JP | 11309185 A | 11/1999 |
| JP | 2001104330 A | 4/2001 |
| JP | 2006518646 A | 8/2006 |
| JP | 2007117532 A | 5/2007 |
| JP | 2007296348 A | 11/2007 |
| JP | 2014515280 A | 6/2014 |
| WO | 2012160134 A1 | 11/2012 |
| WO | 2015189017 | 5/2015 |

\* cited by examiner

ENDOSCOPIC CUTTING DEVICE HAVING A CUTTING WIRE DIRECTED THROUGH OPENINGS IN A TUBE TO FORM TWO DIATHERMY BLADES, AND A PROBE FOR A PERCUTANEOUS ENDOSCOPIC GASTROSTOMY

The present application is a 371 of International application PCT/DE2016/100038, filed Jan. 30, 2016, which claims priority of DE 10 2015 102 542.6, filed Feb. 23, 2015, the priority of these applications is hereby claimed and these applications are incorporated herein by reference.

BACKGROUND OF THE INVENTION

The invention relates to an endoscopic cutting device for cutting free a probe provided with a retaining plate, which, within the scope of a percutaneous endoscopic gastrostomy, is arranged in a stomach wall and is overgrown with gastric mucosa, wherein, for the adjustment of the cutting element provided at a distal end of a tube, an actuation force of a proximally arranged actuation element can be transmitted to said element via a pulling cord arranged in a lumen of the tube, wherein the cutting device comprises an electrically heatable cutting wire which is connected to the pulling cord and is fixed at a first distance to the distal end on the tube and extends from this outside of the tube via a distal section and is introduced into the lumen through a first opening that is provided on the tube at a second, longer distance to the distal end of the tube, so that, when the pulling cord is tightened, the section of the tube is deformed into an arc-shape and the cutting wire forms a first chord-like diathermy blade extending between the first opening and its fixing position on the tube.

The invention further relates to a probe for a percutaneous endoscopic gastrostomy with a hollow cylindrical probe body which is configured together with a retaining plate for bearing against a stomach wall, and after being overgrown with the gastric mucosa will be removed from this through radial cuts executed with an endoscopic cutting device, wherein, for the adjustment of the cutting element provided at a distal end of a tube, an actuation force of a proximally arranged actuation element can be transmitted to said element via a pulling cord arranged in a lumen of the tube, wherein the cutting device comprises an electrically heatable cutting wire which is connected to the pulling cord and is fixed at a first distance to the distal end on the tube and extends from this outside of the tube via a distal section and is introduced into the lumen through a first opening that is provided on the tube at a second, longer distance to the distal end of the tube, so that, when the pulling cord is tightened, the section of the tube is deformed into an arc-shape and the cutting wire forms a first chord-like diathermy blade extending between the first opening and its fixing position on the tube.

In percutaneous endoscopic gastrostomy, the patient is provided with an artificial entrance (PEG probe) through the abdominal wall and the stomach wall into the interior of the stomach to enable feeding him with probe nutrition. The probe body has a tubular or hose-shaped configuration and comprises a retaining plate arranged on the stomach wall, which plate fixes the PEG probe in order to prevent an outward movement of the probe. Normally, this retaining plate bears loosely against the stomach wall and, through this artificial entrance, the PEG probe remains functional throughout the long period of time needed for the required feeding. But to assure this, it is also necessary to mobilize the probe about three days after installation and to repeat this procedure regularly at short intervals.

However, in case of failure to mobilize the probe regularly or due to a permanent traction force applied to the PEG probe, the retaining plate is pressed accordingly against the stomach wall and a burying of the retaining plate can occur because this is then overgrown with gastric mucosa. This complication, in the course of which inflammations can also occur, is called "buried bumper syndrome". In the final analysis, the overgrowing of the retaining plate leads relatively often to a dysfunction of the probe i.e. the proliferating gastric mucosa gives rise to a blocking of the PEG probe. In some cases it is necessary to remove the PEG probe overgrown with gastric mucosa and replace it with a new one.

Various therapeutic methods are available for the removal of the PEG probe. The PEG probe can be removed by surgical intervention which is accompanied by a very heavy burden for the already severely weakened patient. In the case of a laparoscopic surgery, the retaining plate is laid free from the outside by surgical steps using a laparoscope introduced into the interior of the stomach through a created access. The pulling method in which the probe is removed outwards through traction can also be used in connection with laparoscopic surgery.

In the pushing method, to begin with, a guide wire is inserted into the at first shortened PEG probe following which, an endoscopic cutting device configured as a papillotome is positioned in the region of the retaining plate via the guide wire. Using the endoscopic cutting device actinomorphic incisions are made in the overgrown regions of the retaining plate. Following this, the PEG probe is pressed into the interior of the stomach with help of a bougie. Thereafter, the shortened PEG probe can be removed out of the stomach via the gullet with help of endoscopic instruments, for example a gripper or a snare.

An endoscopic cutting device for cutting free a probe provided with a retaining plate of the type stated in the preamble of patent claims 1 and 10, which is arranged in the scope of a percutaneous endoscopic gastrostomy in the stomach wall and is overgrown with the gastric mucosa, is disclosed as prior art in the document Cyrany J. et al; New technique for release of a buried bumper . . . ; Endoscopy 2012; 44; E422-E423 as also in the document Müller-Gerbes D. et al; Management for Buried Bumper Syndrome . . . ; Z. Gastroenterol 2009; 47; 1145-148. In both these documents the respective push method explained above is described in which a papillotome is used as an endoscopic cutting device which is usually provided for opening the papilla vateri for facilitating the removal of gall stones. The papillotome is inserted via the PEG probe into the stomach. Following this, the papillotome is tightened so that its distal end section takes an arch shape that is spanned by a cutting wire. This cutting wire comes to bear convexly against the tissue overgrowing the retaining plate and can, when turned in all directions, make actinomorphic cuts. Following this, the retaining plate is removed from the mucosa bed with a bougie.

SUMMARY OF THE INVENTION

The object of the present invention is to provide a cutting device for treating the buried bumper syndrome that can be used for the pushing method and with which a number of actinomorphic cuts can be made through the overgrown regions right to the internal retaining plate of the PEG probe.

According to the invention, to form a tip, the distal end of the tube is slanted at an angle to the transverse plane thereof, wherein the tip is turned towards the first diathermy blade. With the first distance to the end of the tip, a second opening is formed in the tube through which opening the cutting wire is inserted into the lumen and extends in this up to the tip. Following this, for forming a second diathermy blade, the cutting wire is guided around the tip and along an outer peripheral surface of the tube, back into the tube through the second opening. At least in the region of a section of the tube situated between the two openings, the tube is made of a soft flexible, elastically deformable plastic material.

The electrically heatable cutting wire thus extends not only between the two openings provided in the tube but it also emerges at the distal end of the tube out of the lumen, is arranged around the tip and extends externally along the tube in an axial direction of the tube to re-enter the lumen through the opening provided in the distal end section. Furthermore, the tip that enables a defined immersion of the cutting wire starting therefrom into the overgrown area and thus also a precise guidance of the cutting device, is configured as a slant of the front end face. This further active section of the cutting wire thus serves as a second diathermy blade. Because the section of the tube situated between the two openings is deformed into an arc-shape during a cutting operation in which the tube sections are bent at 180° to each other, it is of particular importance, that the tube, at least in this region of its section situated between the two openings, be made of a soft flexible, elastically deformable plastic material. As already described above, during the endoscopic cutting free of the retaining plate, numerous actinomorphic cuts are made, so that the section has to be extremely deformed several times and then, for pivoting the cutting device, it must return into an only slightly angled position.

In contrast to the above, the cutting device for the push method according to the publications Cyrany J. et al; New technique for release of a buried bumper . . . ; Endoscopy 2012; 44; E422-E423 as also Müller-Gerbes D. et al; Management for Buried Bumper Syndrome . . . ; Z. Gastroenterol 2009; 47; 1145-148, is made as a usual papillotome. This does not have a distal tip created by a slant. Further, a distal end of the cutting wire is fixed on the tube and thus does not extend from the distal end of the tube in axial direction along the outer peripheral surface of the tube. For this reason, it is not possible to make a cut around an extension reaching from the distal end of the PEG probe to the retaining plate. The distal end section of the tube is only bent to a small extent so that it can also have a relatively stiff configuration.

For guiding the cutting wire extending from the tip in axial direction, the hose can comprise a longitudinal groove in its cross-section. Further, it is also possible to provide the tube with flattened areas on both sides of this longitudinal groove, these flattened areas tapering towards each other at an acute angle. This leads to the formation of a wedge shape in this cutting region that makes it possible to push aside the already severed tissue. Thus, place is created for a defined and clean embedding of the cutting wire into the targeted tissue. The tube is made preferably of a fluoropolymer, a polyamide or a polyolefin. The tube can be configured with two lumens, wherein a stranded wire of the cutting wire and, as stated later, a PEEK hose and PEEK sleeves extend in the interior of one of the lumens. Via the second lumen, the cutting device can be guided on a guide wire when being inserted into the PEG probe. In addition, a rinsing liquid can be supplied through the second lumen to the distal end of the cutting device.

According to a further feature of the invention, a distal end section of the cutting wire within the lumen should extend over at least 50% of the region situated between the two openings. The cutting wire guided back in proximal direction in the lumen assists in the re-positioning of the tube when the pulling cord is relaxed with help of the activation element, and thus acts as a spring element. The distal end section within the lumen can then extend up to the first opening.

In addition, the distal end of the cutting wire is to be bent through approximately 180° in order to fix it to the peripheral surface of the lumen. The corresponding end of the cutting wire is bent through ca 180° at an end spacing of about 3 mm so that this end has the effect of a barbed hook acting within the lumen. By reason of the corresponding cutting wire guidance and fixture no further components and no joining and fixing steps are required.

According to another feature of the invention, adjacent to the openings and outside of the region situated between the openings, PEEK sleeves are inserted into the lumen. A first one of the PEEK sleeves may extend in the interior of the lumen from the tip to the second opening. Before the cutting wire exits the lumen through the first or second opening, the lumen is reinforced with a respective PEEK sleeve so that the tube cannot crack or tear in this region. The two PEEK sleeves are clamped within the lumen. With help of the first PEEK sleeve the tube is reinforced at a distal end section thereof i.e. between the tip and the second opening, so that the tube cannot crack or tear in the deflection region of the cutting wire at the tip, and, for penetration into the overgrown regions, the distal end section of the tube has a stiff configuration. Polyetheretherketone (abbreviated: PEEK) is a high temperature-resistant thermoplastic and belongs to the material group of polyaryletherketones. The sleeves may also be made of another tear-resistant plastic or of a metallic material.

In order to make the tube partially stiff against bending and rotation, a PEEK hose extending within the lumen is provided, which hose is fixed with its proximal end in a reception of a guide shaft of the actuation element and bears distally against a front end face of a second PEEK sleeve, this second PEEK sleeve extending up to the first opening. Within the lumen, the PEEK hose is arranged to extend from a guide shaft of the actuation element up to the second PEEK sleeve and serves to enhance the flexural resistance and torsional stiffness of the tube. It is only the region of the tube situated between the two openings that should be flexible and relatively soft that bends into an arc-shape when the pulling cord is tightened. By reason of the torsional stiffness, rotary movements on the actuation element can be transmitted without delay to the cutting device.

According to a further feature of the invention, the actuation element should comprise a guide shaft that is at least indirectly connected to the tube and a pushing element acting on the pulling cord, an element for triggering a haptic signal, which is triggered when the cutting device has reached one of its cutting positions, being situated between the guide shaft and the pushing element. From this signal the surgeon can discern whether the cutting device is situated in one of its cutting positions. The signal can be triggered for example when the tip is situated in the region of an edge of the retaining plate, because at this moment, the cutting wire can be energized, or at a maximum bending of the tube, be moved to an outer periphery of a hub of the retaining plate. The element for triggering the haptic signal can be configured as a catch groove on an outer peripheral surface of the pushing element and a spring-loaded ball extending radially to the catch groove in the pushing element.

Finally, the probe for the percutaneous endoscopic gastrostomy is to be provided with a hollow cylindrical probe body, which is configured together with a retaining plate for bearing against a stomach wall, and after being overgrown with the gastric mucosa will be removed from the stomach wall through radial cuts executed with an endoscopic cutting device. For adjustment of the cutting device provided at a distal end of a tube, an actuation force of a proximal actuation element can be transmitted to this via a pulling cord. The pulling cord is guided in the lumen of a tube, wherein the cutting device comprises an electrically heatable cutting wire which is fixed with a first distance to the distal end on the tube and extends from this, outside of the tube over a distal section and is introduced into the lumen through a first opening provided in the tube, which opening has a second, longer distance to the distal end of the tube. Thus, when the pulling cord is tightened, the section of the tube is deformed into an arc-shape and the cutting wire forms a first chord-like diathermy blade extending between the first opening and its fixing position on the tube.

A distal end of the probe body that comprises an axial overhang relative to the retaining plate is adapted with regard to its axial and radial dimensions to the position of the cutting wire and the position of a distal end configured as a tip of the tube, which positions these take during a cutting procedure. The cutting wire length and the distance of the tip to the center of the arc-shaped deformation of the tube adapted to the dimensions of the retaining plate and the hub of the probe effectuate that the cutting device acts from above directly on the edge of the hub. Upon a further tightening of the pulling cord, the tip surrounded by the second diathermy blade moves slowly in direction of the center of the PEG probe. In the fully tightened position of the tube, the hub of the PEG probe is completely surrounded by the cutting wire, i.e. both in axial and in radial direction, so that a cut has been executed.

In addition to this, other possibilities arise of combining with each other also individual features as far as they result from the patent claims, the described advantages of the patent claims, the following description of the examples of embodiment, or at least from the drawing. Reference made in the claims to the drawing through the use of reference numerals is in no way meant to limit the scope of protection of the patent claims.

For a further elucidation of the invention reference will be made to the drawing in which one example of embodiment is represented in a simplified manner. The figures show:

BRIEF DESCRIPTION OF THE DRAWING

FIG. 1, a treatment of a buried bumper syndrome using an endoscopic cutting device according to the invention, FIG. 2, a longitudinal section of the endoscopic cutting device used in accordance with FIG. 1, FIG. 3, an enlarged section according to III out of the representation of FIG. 2, showing the region of a first opening provided in a tube through which a cutting wire extends out of a lumen, FIG. 4, an enlarged section according to IV out of the representation of FIG. 2, showing a guide shaft of an actuation element on which the tube as also a PEEK hose are fixed, FIG. 5, a longitudinal section of a partial view of the cutting device in the region of a distal end thereof, FIG. 6, a partial longitudinal section of an actuation element of the cutting device, FIG. 7, an enlarged section according to VII out of the representation of FIG. 6, showing an arrangement for creating a haptic signal, FIG. 8, an alternative form of embodiment of the distal end section, wherein, in this region, the tube is provided with flattened regions and thus has a wedge-like configuration, FIG. 9, a longitudinal section of the cutting region of the cutting device, FIG. 10, a longitudinal section through a PEG probe with a cutting device arranged therein, which, in this case, is in a stretched state, FIG. 11, the state of the cutting device in which the tube is bent that far that the cutting wire is bent at an angle of about 45° at the first opening, FIG. 12, the state of the cutting device in which the tube is bent that far that the distal end section thereof extends at an angle of about 180° to the proximal section, wherein the tip of the tube acts on the edge of a retaining plate, and FIG. 13, the state of the cutting device in which the tube is bent that far that the distal end section thereof extends at an angle of about 180° to the proximal section, wherein the tip has been guided up to a hub provided on the retaining plate.

DETAILED DESCRIPTION OF THE INVENTION

Figure 1:
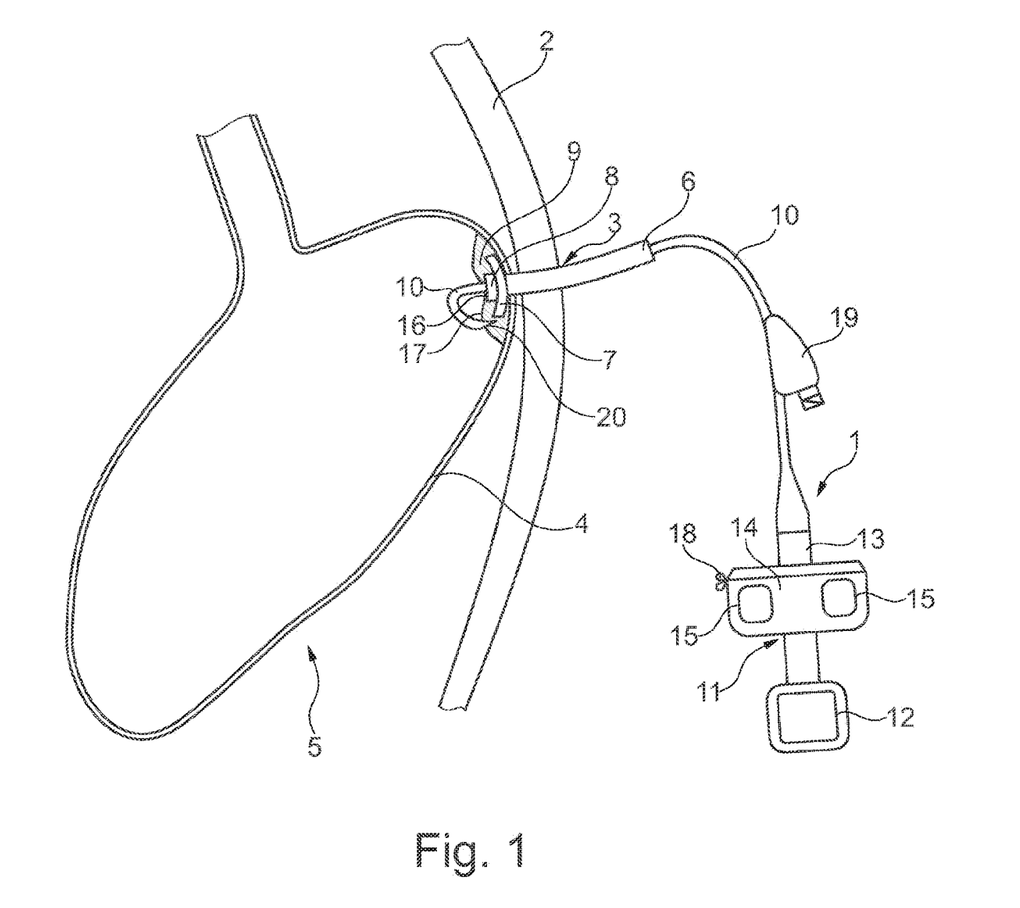

In FIG. 1, an endoscopic cutting device which is intended for treating a buried bumper syndrome is identified at 1. A PEG probe 3 for feeding the patient is inserted into the abdominal wall 2 of the patient and extends through a stomach wall 4 of a stomach 5. The PEG probe 3 comprises a hollow cylindrical probe body 6 preferably configured as a hose and further comprises an inner retaining plate 7 connected to the probe body 6, which retaining plate 7 bears, in the interior of the stomach 5, against the stomach wall 4 so that the PEG probe 3 is fixed. The probe body 6 extends beyond the retaining plate 7 thus forming a hub 8. As further disclosed in FIG. 1, on its surface turned towards the interior of the stomach, the retaining plate 7 is overgrown with gastro mucosa 9, in other words embedded in the stomach wall 4. This means that centers of inflammation can form in the region of this overgrowth and lead to considerable problems in the removal of the PEG probe out of the stomach wall or the abdominal wall 2.

For cutting free the retaining plate 7, the endoscopic cutting device 1 is inserted through the PEG probe 3 into the interior of the stomach 5. The cutting device comprises a tube 10 made of a soft, flexible plastic material on whose proximal end an actuation element 11 is arranged. With this actuation element 11 that comprises a guide shaft 13 connected to a thumb ring 12 and a pushing element 14 with two finger rings 15 configured thereon, a distal end section of the tube 10 can be tightened into an arc-shape such that a cutting wire 16 spanning this arc acts as a first diathermy blade 17 that is energized and thus heated through a high frequency electrical connection 18. In addition, a sluice 19 is provided on the tube 10 through which sluice 19, a guide wire and/or a rinsing liquid can be fed which, via a lumen described in connection with FIGS. 2, 5 and 9, extend or are directed up to the distal end of the tube 10. At its distal end, the tube 10 is provided with a tip 20 which, in the arc-shaped bent position of the end region that is shown in FIG. 1, pierces the gastro mucosa 9 overgrowing the retaining plate 7.

Figure 2:
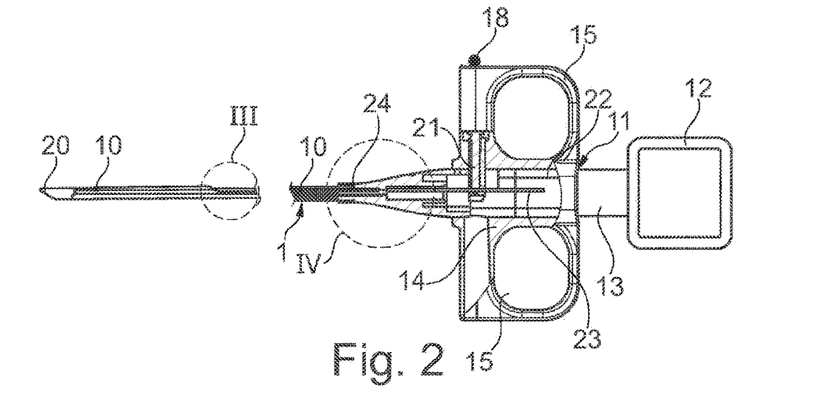

In FIG. 2, the endoscopic cutting device 1 is shown in a stretched state, in which it is situated for example before the distal end thereof is inserted into a PEG probe 3 according to FIG. 1. The details of the cutting device 1 already explained in connection with FIG. 1 and also shown in FIG. 2, bear the same reference numerals. Additionally, FIG. 2 also discloses that an entraining element 21 projects radially inwards from the pushing element 14 and is guided in a longitudinal slit 22 of the guide shaft 13. On this entraining element is fixed a pull rod 23 which connects further on to a pulling cord 24.

Figure 3:
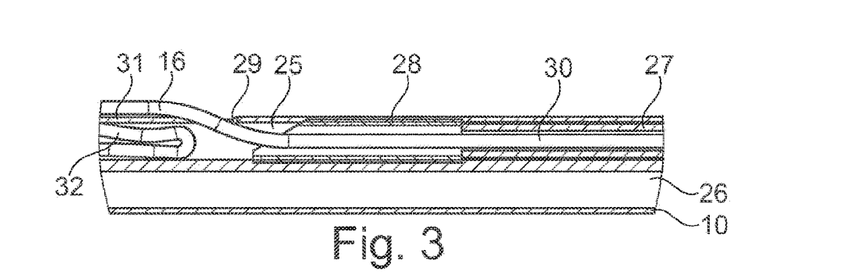

A first enlarged section III out of FIG. 2 is represented in FIG. 3. This shows a partial section of the tube 10 with a first lumen 25 extending in the tube 10, as well as a second lumen 26. In the first lumen 25 a PEEK hose 27 is arranged proximally and, as will be shown later in subsequent figures, reaches up to the guide shaft 13 of the actuation element 11. With help of the PEEK hose 27 the tube 10, which as a whole is soft and flexible, is partially stiffened, so that sliding and rotational movements generated by the actuation element 11 can be transmitted through this to the distal end section of the tube 10.

In distal direction, within the first lumen 25, the PEEK hose 27 is followed by a second PEEK sleeve 28 which ends distally at a slant in front of a first opening 29. The slanted end of this second PEEK sleeve 28 is oriented such that it tapers towards the first opening 29. Within the PEEK hose 27 and the second PEEK sleeve 28 extends the stranded wire 30 which serves as a cutting wire 16 and is connected proximally to the pulling cord 24. The cutting wire 16 emerges out of the first opening 29 from the PEEK sleeve 28 and the first lumen 25 respectively and extends along an outer peripheral surface 31 of the tube 10. The further course of the cutting wire 16 of which an end 32 bent around through 180° is shown in FIG. 3, can be seen in some of the figures described in the following. FIG. 3 discloses that the end 32 extends up to the first opening 29 and is configured such that it hooks firmly into the first lumen 25 under traction force.

Figure 4:
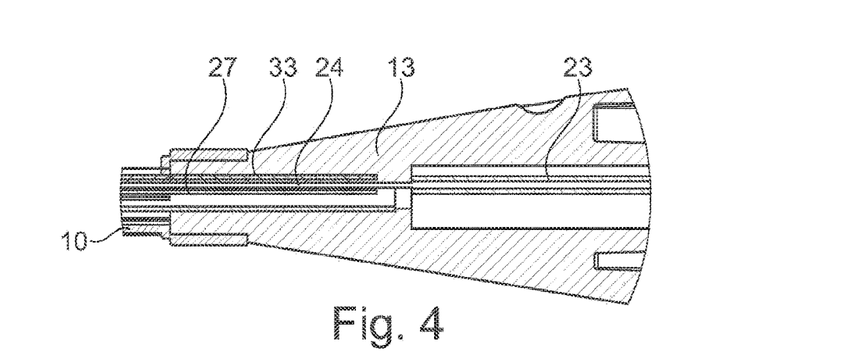

A second enlarged section IV out of FIG. 2 that shows the connection of the guide shaft 13 to the tube 10 as also to the PEEK hose 27 is illustrated in FIG. 4. It can be seen in this figure that the PEEK hose 27 guided in the first lumen 25 is fixed in a reception 33 of the guide shaft 13. The pulling cord 24 extending within the PEEK hose 27 is fixed in the pull rod 23.

Figure 5:
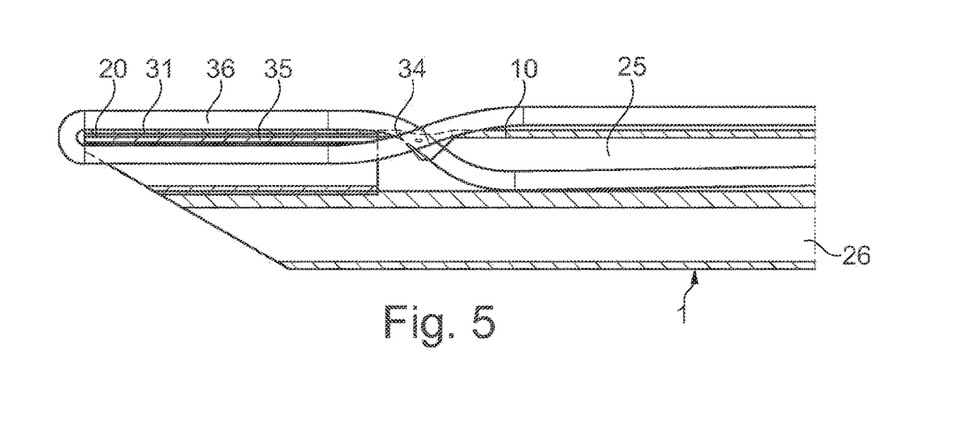

In FIG. 5 is shown a distal end of the cutting device 1 with the tip 20 which is made by severing the tube 10 at an angle to the transverse plane. At a distance to this tip 20, a second opening 34 is provided in the tube 10 which merges into the first lumen 25. Starting from the distal end of the tube 10, is situated in the lumen 25, a first PEEK sleeve 35 that reaches proximally up to the second opening 34. In addition, the complete course of the cutting wire 16 in the region of the two openings 29 and 34, as also of the tip can be seen in FIG. 9. As shown in the figure, the cutting wire 16 extending along the outer peripheral surface 31 is to be guided through the second opening 34 into the first lumen 25 in which it extends up to the tip 20.

Figure 9:
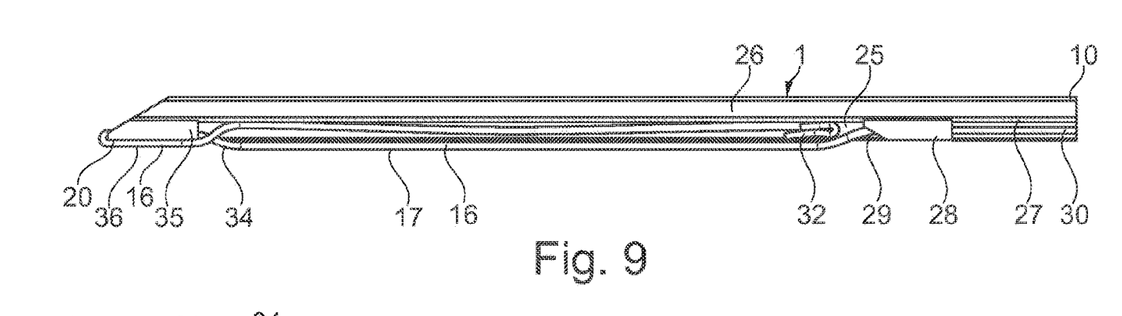

At the tip 20, the cutting wire 30 is deflected around through 180° and extends then forming a second diathermy blade 36, once again along the outer peripheral surface 31 up to the second opening 34 to re-enter the first lumen 25 at this opening. As can be seen from FIGS. 3 and 9, this end section of the cutting wire 16 extending in proximal direction is provided with the end 32 bent around through 180°. FIG. 9 shows that the end section extends over the region situated between the two openings 29 and 34.

Figure 6:
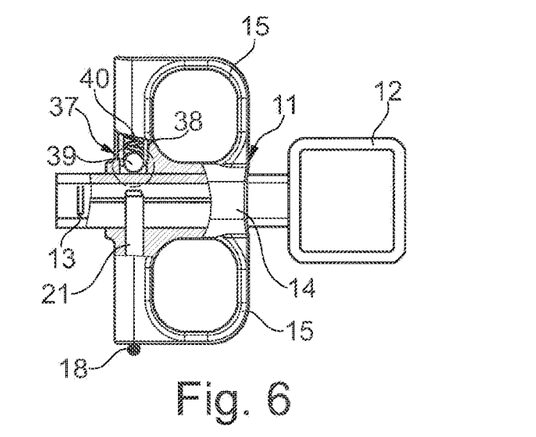
Figure 7:
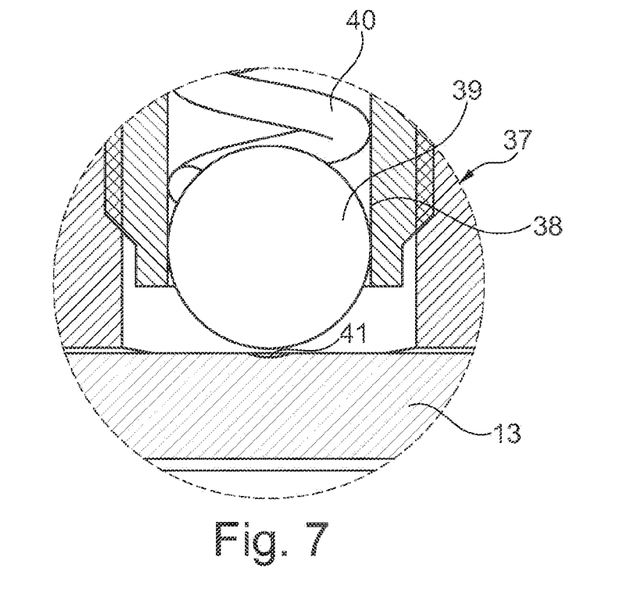

FIG. 6 shows the actuation element 11 which, in this case, is provided with an element 37 for generating a haptic signal. For this purpose, a ball 39 is arranged in a radially extending bore 38 of the pushing element 14. An enlarged section VII out of FIG. 6, showing the configuration of the element 37 for generating a haptic signal is illustrated in FIG. 7. For elucidating the function of this element 37, the ball 39 that is loaded by a compression spring 40 is shown in a position in which the ball 39 is raised from the guide shaft 13, so that a catch recess 41 arranged on the guide shaft 13 is visible. The ball 39 snaps into this catch recess 41 when the cutting device 1 is situated in a cutting position which the treating surgeon perceives at the actuation element 11.

Figure 8:
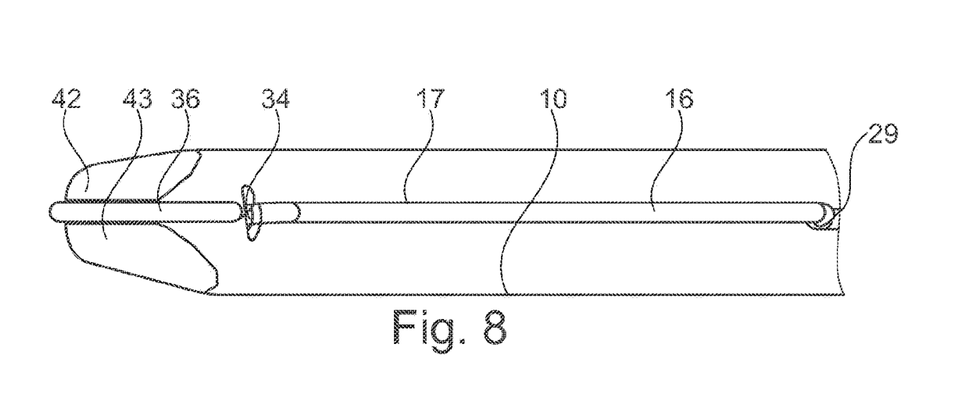

In FIG. 8 is illustrated a distal end section of a further example of embodiment of the endoscopic cutting device 1 in which, on its end section comprising the tip 20, the tube 10 is provided at least partially with slanted portions 42 and 43, so that the tube 10 is given a wedge-shaped configuration in this region. For this reason, the portions of the gastro mucosa separated from each other are pressed apart during the cutting operation of the second diathermy blade 36.

Figure 10:
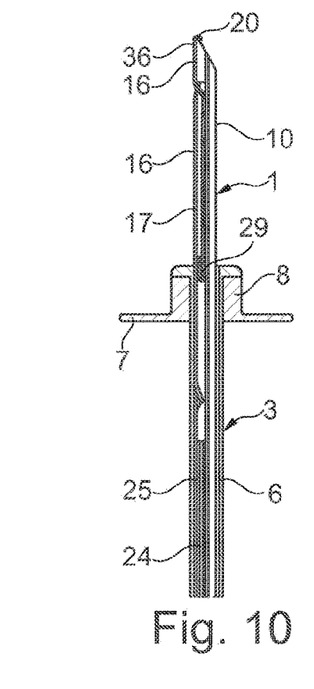
Figure 11:
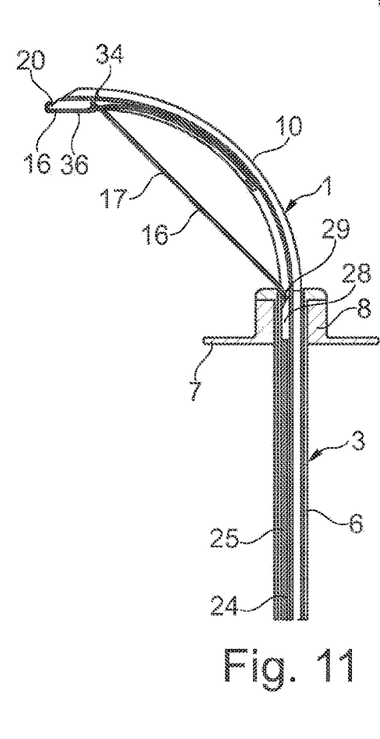

In FIGS. 10 to 13 the endoscopic cutting device which is inserted into the PEG probe 3 is illustrated in its different positions. As already described in connection with FIG. 1, the PEG probe 3 comprises the retaining plate 7, the hub 8 extending from this into the interior of the stomach, and the probe body 6 configured as a hose. FIG. 10 shows the cutting device 1 in its stretched state after it has been inserted into the PEG probe 3. According to FIG. 11, due to an angular bending of the tube 10 through approximately 90°, the cutting wire 16 extends at an angle of 45°. For this reason, with the help of the cutting wire bearing against the end of the hub 8, the cutting device 1 comes to be oriented in axial direction.

Figure 12:
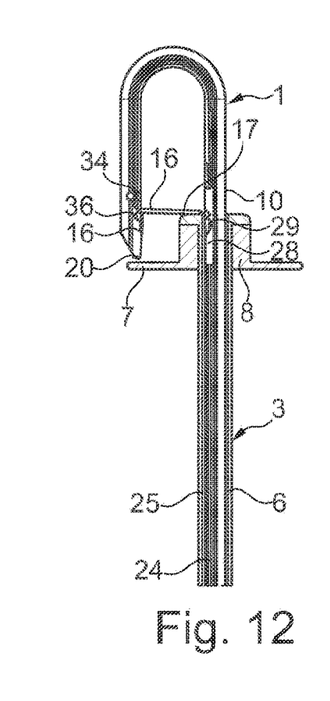
Figure 13:
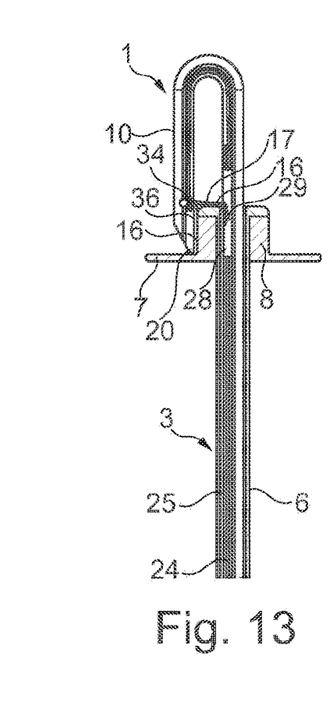

According to FIG. 12, the pulling cord is tightened such that the distal end section of the tube 10 is bent through 180° and thus extends parallel to the rest of the tube 10. In this way, the tip 20 together with the cutting wire 16 guided around this, is applied to the edge of the retaining plate 7. This position is communicated through a signal as described in connection with FIGS. 6 and 7 to the surgeon and he turns on the high frequency current. Following this, he tightens the pulling cord further and an actinomorphic cut is performed via the retaining plate 7, wherein both the first diathermy blade 17 and the second diathermy blade 36 are active.

After relaxation of the pulling cord and a respective turning of the cutting device 1, the cuts are repeated many times. Because the tube 10 has a soft elastic configuration in its bending region and is flexible due to the cutting wire 16 being guided backwards within the lumen 25, on the one hand, the tube 10 can be bent very strongly at an angle and returns on the other hand, again into its former position. The PEEK sleeves 28 and 35 prevent the tube 10 from tearing or cracking in the region of the openings 29 and 34.

LIST OF REFERENCE NUMERALS 1 endoscopic cutting device
2 abdominal wall
3 PEG probe
4 stomach wall
5 stomach
6 probe body
7 retaining plate of 3

8 hub of 3
9 gastro mucosa
10 tube
11 actuation element
12 thumb ring of 11
13 guide shaft of 11
14 pushing element of 11
15 finger ring
16 cutting wire
17 first diathermy blade
18 high frequency connection
19 sluice
20 tip
21 entraining element
22 longitudinal slit
23 pull rod
24 pulling cord
25 first lumen
26 second lumen
27 PEEK hose
28 second PEEK sleeve
29 first opening
30 stranded wire
31 outer peripheral surface of 10
32 end of 16
33 reception in 13
34 second opening
35 first PEEK sleeve
36 second diathermy blade
37 element
38 bore
39 ball
40 compression spring
41 catch recess

The invention claimed is:

1. An endoscopic cutting device for cutting free a probe provided with a retaining plate, which, within the scope of a percutaneous endoscopic gastrostomy, is arranged in a stomach wall and is overgrown with gastric mucosa, wherein the cutting device comprises: a tube having a lumen and a distal end; a cutting element provided at the distal end of the tube; a pulling cord arranged in the lumen of the tube and attached to the cutting element; and an actuation element arranged proximally on the pulling cord so that an actuation force of the actuation element can be transmitted to said cutting element via the pulling cord; the cutting element including an electrically heatable cutting wire which is connected to the pulling cord and is fixed at a first distance to the distal end on the tube and extends from a fixing position outside of the tube via a distal section and is introduced into the lumen through a first opening provided on the tube at a second, longer distance to the distal end of the tube, so that, when the pulling cord is tightened, the section between the first opening of the tube and the fixing position is deformed into an arc-shape and the cutting wire forms a first chord-like diathermy blade extending between the first opening and its fixing position on the tube, wherein the distal end of the tube is slanted at a plane transverse to a longitudinal extension of the tube so as to form a tip, wherein the tip is aligned in a direction of the first diathermy blade, that, with a first distance to the end of the tip, a second opening, aligned in the direction of the tip, is formed in the tube, through which opening, the cutting wire is inserted into the lumen and extends in the lumen up to the tip, that, for forming a second diathermy blade, the cutting wire is made to extend outside around the tip and along an outer peripheral surface of the tube through the second opening into the tube, and that, in the region of a section of the tube situated between the two openings, the tube is made of a soft flexible, elastically deformable plastic material, wherein, adjoining the openings and outside of the region situated between the openings, PEEK sleeves are arranged inside the tube.

2. The endoscopic cutting device of claim 1, wherein a distal end section of the cutting wire within the lumen extends over at least 50% of the region situated between the two openings.

3. The endoscopic cutting device of claim 2, wherein the distal end section within the lumen extends up to the first opening.

4. The endoscopic cutting device of claim 1, wherein the distal end of the cutting wire is bent through approximately 180° for fixing this on the peripheral surface of the lumen.

5. The endoscopic cutting device of claim 1, wherein PEEK sleeves are inserted into the lumen.

6. The endoscopic cutting device of claim 5, wherein a first PEEK sleeve extends within the lumen from the tip up to the second opening.

7. The endoscopic cutting device of claim 5, wherein a PEEK hose extending within the lumen is fixed with a proximal end thereof in a reception of a guide shaft of the actuation element and bears distally against a front end face of a second PEEK hose that extends up to the first opening.

8. The endoscopic cutting device of claim 1, wherein the actuation element comprises a guide shaft that is connected at least indirectly to the tube and a pushing element that acts on the pulling cord, an element for triggering a haptic signal which is triggered when the cutting device has reached one of its cutting positions being arranged between guide shaft and pushing element.

9. The endoscopic cutting device of claim 8, wherein the element for triggering the haptic signal is configured as a catch recess on an outer peripheral surface of the guide shaft and as a spring-loaded ball extending in the pushing element radially relative to the catch recess.

10. A combination, comprising:
a probe for a percutaneous endoscopic gastrostomy with a hollow cylindrical probe body, a retaining plate and a hub projecting distally axially beyond the retaining plate, the probe body and the retaining plate being configured for bearing against a stomach wall; and
an endoscopic cutting device arrangeable in the hollow cylindrical probe body for executing radial cuts to remove the probe from the stomach wall after the probe is overgrown with gastric mucosa, wherein the cutting device comprises a tube having a lumen and a distal end with a tip, a cutting element provided at the distal end of the tube, a pulling cord arranged in the lumen of the tube and attached to the cutting element, and an actuation element arranged proximally on the pulling cord so that an actuation force of the actuation element can be transmitted to said cutting element via the pulling cord, the cutting element including an electrically heatable cutting wire which is connected to the pulling cord and is fixed at a first distance to the distal end on the tube, passes through a second opening and extends from the second opening outside of the tube via a distal section and is introduced into the lumen through a first opening provided on the tube at a second, longer distance to the distal end of the tube, so that, when the pulling cord is tightened, the section of the tube between the first opening and a fixing position is deformed into an arc-shape and the cutting wire forms a first chord-like diathermy blade extending between the first opening and its fixing position on the tube, wherein at least in the region of a section of the tube situated between the two openings, the cutting wire passes into the lumen through the second opening and extends in the lumen up to the tip, for forming a second diathermy blade the cutting wire is extendable outside around the tip and along an outer peripheral surface of the tube, and through the second opening into the tube, the tube is made of a soft flexible, elastically deformable plastic material, wherein the hub has axial and radial dimensions adapted to a position of the second diathermy blade in relation to the tip and a length of the second diathermy blade and to the position of the tip, which positions the second diathermy blade and the tip take during use.

* * * * *